US008038648B2

(12) United States Patent
Marksteiner

(10) Patent No.: US 8,038,648 B2
(45) Date of Patent: Oct. 18, 2011

(54) INJECTION DEVICE AND METHOD

(75) Inventor: Rainer Marksteiner, Schwaz (AT)

(73) Assignee: Innovacell Biotechnologie GmbH, Innsbruck (AT)

( * ) Notice: Subject to any disclaimer, the term of this patent is extended or adjusted under 35 U.S.C. 154(b) by 0 days.

(21) Appl. No.: 11/916,184

(22) PCT Filed: Jun. 2, 2006

(86) PCT No.: PCT/EP2006/005286
§ 371 (c)(1),
(2), (4) Date: Jul. 7, 2008

(87) PCT Pub. No.: WO2006/128718
PCT Pub. Date: Dec. 7, 2006

(65) Prior Publication Data
US 2009/0234319 A1 Sep. 17, 2009

(30) Foreign Application Priority Data
Jun. 3, 2005 (DE) .......................... 10 2005 025 639

(51) Int. Cl.
*A61M 5/00* (2006.01)
*A61M 31/00* (2006.01)
*A61M 1/00* (2006.01)
(52) U.S. Cl. ......... 604/117; 604/506; 604/118; 604/181
(58) Field of Classification Search ................. 604/117, 604/506, 272, 521, 239, 116, 500, 181, 507, 604/19, 48; 600/459, 461, 463, 437
See application file for complete search history.

(56) References Cited

U.S. PATENT DOCUMENTS

| 4,535,781 | A | * | 8/1985 | Hetz .............................. 600/459 |
| 4,892,520 | A | | 1/1990 | Gilbaugh et al. |
| 4,900,303 | A | | 2/1990 | Lemelson et al. |
| 5,141,496 | A | * | 8/1992 | Dalto et al. ................... 604/117 |
| 5,211,176 | A | * | 5/1993 | Ishiguro et al. ............... 600/463 |
| 5,465,724 | A | * | 11/1995 | Sliwa et al. ................... 600/459 |
| 6,095,981 | A | | 8/2000 | McGahan |

(Continued)

FOREIGN PATENT DOCUMENTS
DE 100 58 370 A1 6/2002
(Continued)

OTHER PUBLICATIONS

English Translation of International Search Report, Issued by the European Patent Office on Sep. 6, 2006 for corresponding PCT Application No. PCT/EP2006/005286.

*Primary Examiner* — Theodore J Stigell
*Assistant Examiner* — Bradley G Thomas, Jr.
(74) *Attorney, Agent, or Firm* — Duane Morris LLP

(57) ABSTRACT

An injection device (100) for injecting a substance into an organism (1) is described, comprising a guide device (10) with a lumen (11) in which an injection tool (21) is arranged in a displaceable manner, a displacement device (20) to which the injection tool (21) is connected, and a holder device (30) that forms a support for the guide and displacement devices (10, 20), said guide and displacement devices (10, 20) being displaceably arranged on the holder device (30). A method for injecting a substance into an organism (1) is also described.

23 Claims, 3 Drawing Sheets

U.S. PATENT DOCUMENTS

| | | | |
|---|---|---|---|
| 6,171,249 B1 * | 1/2001 | Chin et al. ................ 600/461 |
| 6,309,374 B1 * | 10/2001 | Hecker et al. ............. 604/117 |
| 2001/0049496 A1 | 12/2001 | Kirchhofer et al. | |
| 2002/0049385 A1 * | 4/2002 | Booker et al. ............. 600/459 |
| 2004/0092821 A1 * | 5/2004 | Hering et al. ............. 600/459 |
| 2005/0240102 A1 * | 10/2005 | Rachlin et al. ............. 600/437 |

FOREIGN PATENT DOCUMENTS

| | | |
|---|---|---|
| DE | 101 34 911 A1 | 2/2003 |
| EP | 0 956 873 | 11/1999 |
| WO | WO 2006/002343 | 1/2006 |
| WO | WO2006/111861 | 10/2006 |

\* cited by examiner

INJECTION DEVICE AND METHOD

The invention relates to an injection device for injecting a substance into an organism having the features of the preamble of claim 1, in particular to an injection device for injecting a therapeutically effective substance in a targeted manner into the tissue of the organism at a predefined injection site. The invention furthermore relates to an injection method using this injection device.

EP 1 337 183 discloses a medical operating device, by means of which an injection needle can be introduced into a tissue that is to be treated. At an outlet end of the operating device, the injection needle is deflected by an exit angle relative to an axis of the operating device. The depth to which the injection needle penetrates into the tissue depends on the exit length of the tip of the injection needle relative to the outlet end of the operating device. In the prior art, it is provided to monitor the positioning of the injection needle and the injection using an ultrasonic probe. In order to avoid undesirable injury to the tissue, in the prior art the ultrasonic probe is equipped with a stop which prevents any displacement of the injection needle out of the field of view of the ultrasonic probe.

In the prior art according to EP 1 337 183, considerable progress was made in terms of the precise deposition of therapeutically effective substances into a tissue. However, one disadvantage is that there is a fundamental risk of injury because the injection needle can be positioned in a defined manner relative to the ultrasonic probe but not relative to the tissue. During practical use of the conventional operating device, therefore, the following problems may arise. When the needle positioning accuracy is in the mm or sub-mm range, the risk of incorrect positioning or even of injury to the surrounding tissue can be countered only by very carefully observing the ultrasound image and slowly pushing the injection needle forward. However, particularly when injections are to be carried out at several injection sites within one organ, a slow injection process may delay the treatment and may lead to undesirable stress for the person being treated. Moreover, the precise positioning of the injection needle requires a high level of experience and skill of the treating physician.

The method described in EP 1 337 183 is used in particular for the targeted injection of substances into the wall of body cavities or tubes (e.g. the urethra), the sonic probe for displaying the walls being integrated in the injection device or connected to the latter. However, this embodiment may be disadvantageous since the sonic probe or MRI probe takes up space inside the body cavities or the respective body lumen, which may lead to stretching of the surrounding tissue with a potential risk of injury.

The objective of the invention is to provide an improved medical operating device which overcomes the disadvantages of the prior art and which in particular reduces the risk of incorrect positioning and/or injury and makes it possible to accelerate an injection treatment. The objective of the invention is also to provide correspondingly improved methods for injecting substances into an organism.

These objectives are achieved by an injection device and an injection method having the features of claims 1 and 18 respectively. Advantageous embodiments and uses of the invention are defined in the dependent claims.

With regard to the device, the invention is based on the general technical teaching of providing an injection device for injecting a substance into an organism, comprising a displacement device to which an injection tool is connected and a guide device with a lumen for accommodating the injection tool, the displacement device and the guide device being connected to a holder device such that they can be displaced relative to one another. The holder device forms a common support for the guide and displacement devices, which support can be positioned in a stationary manner relative to the organism and in particular to the desired injection site. The injection tool is preferably firmly connected to the displacement device, in particular is attached to the displacement device. Advantageously, the holder device allows reliable and precise adjustment of the guide and displacement devices relative to the organism and relative to one another, so that the injection site in the organism is precisely defined by the position of the two parts which can be adjusted independently of one another. By adjusting the guide and displacement devices on the holder device, the risk of incorrect positioning in the organism is avoided.

The guide device is an elongate component, e.g. a tube or rod, and the lumen for accommodating the injection tool runs in the wall thereof at least over part of the length of the guide device. The guide device extends along a reference line which may be straight or curved depending on the desired use of the injection device. In the first case the guide device has the shape of a straight rod or tube, the reference line corresponding to a longitudinal axis of the guide device, whereas in the second case the shape of a curved rod or tube is provided, the reference line corresponding to a center line of the guide device. At a free end of the guide device pointing away from the holder device, there is provided an outlet end at which the lumen terminates. At the outlet end, the lumen has a predefined angle relative to the reference line extended in a straight line at the outlet end, which reference line represents the shape of the guide device. In the case of a straight guide device, at the outlet end the lumen forms an angle relative to the reference line (longitudinal axis) of the guide device. In the case of a curved shape, at the outlet end the lumen forms an angle with the center line of the guide device extended in a straight line at the outlet end.

At least in the partial region in which the lumen runs, the guide device may be made of a rigid material, e.g. metal (e.g. stainless steel) or plastic (e.g. glass-fiber-reinforced plastics, PVC, PEEK or the like), or of a flexible, in particular elastic material, e.g. plastic (e.g. PMMA).

By means of the displacement device, the injection tool can be displaced inside the lumen of the guide device. The displacement device serves to actuate the injection tool, the following operating positions of the displacement device on the holder device being provided in particular. In a pulled-back operating position of the displacement device, the injection tool is pulled back toward the holder device. In a pushed-forward operating position of the displacement device, the injection tool is pushed forward so that its free end moves away from the holder device and toward the organism. The displacement device can be displaced on a displacement path between the operating positions. The following operating positions are also provided in particular for the guide device. In a pulled-back operating position of the guide device, the latter is pulled back toward the holder device so that the outlet end of the guide device is at a minimum distance from the holder device. Conversely, in a pushed-forward operating position of the guide device, the outlet end is at a maximum distance from the holder device. The guide device can be displaced and fixed on a displacement path between said operating positions.

The adjustment of the guide and displacement devices between said operating positions takes place as a function of the current operating phase of the injection device and the desired depth of penetration of the injection tool into a tissue of the organism. The length of the injection tool, the length of the guide device and the displacement paths of the guide and displacement devices on the holder device are selected in such a way that, in the pulled-back operating position of the displacement device, the injection tool is completely retracted into the lumen of the guide device. This advantageously means that the guide device can be introduced into an organism to be treated, e.g. into a hollow organ of the organism, without any risk of injury.

The adjustment of the guide device between the pulled-back and pushed-forward operating positions defines the position of the outlet end of the guide device relative to the displacement device and thus a free exit length of the injection tool in a pushed-forward operating position of the displacement device. By forming an angle between the end of the lumen and the reference line of the guide device, at the same time a depth of penetration into the tissue of the organism is defined by the exit length of the injection tool, as described in EP 1 337 183. When the guide device is in a pulled-back operating position, a greater exit length of the injection tool and thus a greater depth of penetration are achieved in the pushed-forward operating position of the displacement device than when the guide device is in a pushed-forward operating position.

The injection device according to the invention has the particular advantage that, by adjusting the guide and displacement devices relative to one another on the common support in a predetermined manner, it is possible to define the depth of penetration of the injection tool.

According to a preferred embodiment of the invention, the holder device has a forward stop which limits the forward movement of the displacement device to a maximum value. The position of the forward stop is selected in such a way that, even when the guide device is pulled back, the injection tool does not penetrate into the tissue any deeper than a predefined limit depth. Advantageously, inadvertent injury to adjacent tissue can thus be ruled out. Unlike the conventional medical operating device, in which a stop was provided for the injection tool relative to an ultrasonic probe or to the shaft of the latter and thus only an incorrect position outside the field of view of the ultrasonic probe could be avoided, the forward stop for the holder device makes it possible to limit the movement of the injection tool in the fixed coordinate system of the holder device. The following important advantages of the injection device according to the invention are thus achieved. Firstly, inadvertent injuries to surrounding tissue are ruled out. Secondly, the forward movement of the injection tool to the injection site can take place at a relatively high speed, since it is not possible to inadvertently miss the injection site on account of the forward stop. The injection into the organism becomes faster, which is effective in particular when injecting at a large number of adjacent injection sites, such as e.g. when injecting into the wall of the urethra.

According to a further, preferred embodiment of the invention, the holder device has a backward stop which limits the backward movement of the guide device relative to the holder device. Advantageously, the backward stop can likewise ensure the maximum penetration depth of the injection tool and additionally also the safe retraction of the injection tool into the lumen in the pulled-back operating position of the displacement device. The position of the backward stop is thus preferably selected in such a way that, in the pulled-back operating position of the displacement device, the injection tool is located fully in the lumen of the guide device.

The guide and displacement devices are arranged on the holder device such that they can be displaced in a straight line. To this end, in principle any available linear guide may be used, which is arranged for example on the surface of the holder device. According to one preferred embodiment of the invention however, the holder device has a tubular structure, the guide device being arranged in the interior thereof and the displacement device being arranged on the surface thereof. Provided in the wall of the tubular structure are openings for passing the injection tool through from the displacement device into the lumen of the guide device and possibly for at least one of the forward and backward stops or possibly further adjustment devices. The tubular holder device advantageously allows a compact structure of the injection device, since the guide and displacement devices can be arranged coaxially at least in part-regions. Furthermore, given a straight shape, the tubular structure also allows a rotatability of the guide and displacement devices about a longitudinal axis of the holder device. When the guide and displacement devices are accordingly arranged in a rotatable manner according to one preferred variant of the invention, advantages can be obtained with regard to an injection on all sides through the wall of a hollow organ, such as e.g. the urethra.

Preferably, the injection device is equipped with a rotary bearing, in which the holder device is arranged. The rotary bearing can be positioned in a stationary manner relative to the organism to be treated. The holder device seated in the rotary bearing cannot be displaced relative to the organism. The structure of the holder device with the guide and displacement devices is rotatably arranged in the rotary bearing. When the rotary bearing according to a further variant of the invention is equipped with a mandrel which blocks a rotation of the holder device in the pushed-forward operating position of the displacement device, it is advantageously possible to rule out an inadvertent rotation while the injection tool is projecting from the guide device and thus to rule out injury to the organism. Preferably, the displacement device has a perforated ring which cooperates with the mandrel of the rotary bearing. The perforated ring contains a number of guide holes, which allows a forward movement of the displacement device in predefined angular positions.

Advantageously, the number and/or angular distribution of the guide holes is selected as a function of the desired geometric distribution of injection sites in the organism. The perforated ring thus defines a mask which allow a reliable, radially complete injection into the wall of a hollow organ.

Further advantages for the reliability and reproducibility of the choice of injection site can be obtained if the movement of the guide device relative to the holder device can be blocked. A releasable fixing of the guide device to the holder device is provided. Preferably, to this end, use is made of a first clamping device which can fix the position of the guide device on the holder device between the pushed-forward and pulled-back operating positions. If the first clamping device used is a clamping screw which is inserted into the body of the guide device from outside through a slot in the wall of the tubular holder device, advantages can be obtained for simplified operation and adjustment of the guide device. With particular preference, the clamping screw has an internal flushing channel, through which a flushing fluid can be introduced into a channel in the guide device.

For practical use of the injection device according to the invention, said injection device is preferably equipped with an imaging probe, such as e.g. an ultrasonic probe or an MRI probe, for monitoring the movement of the injection tool in the organism and/or the injection of a substance at the injection site. Preferably, the guide device has an internal channel in which the imaging probe can be arranged, so that the active part, e.g. the ultrasonic transducer, projects from the channel at the outlet end of the guide device. The imaging probe may be fixedly connected to the guide device. However, advantages with regard to the flexibility of use of the injection device are obtained if the imaging probe is arranged in a displaceable manner in the channel of the guide device, in order to be able to be adapted to the current position of the guide device and of the displacement device. When, according to one preferred variant, a second clamping device is provided which can be used to fix the probe relative to the guide device, advantages are obtained with regard to the reliability of monitoring the injection.

According to the invention, the displacement device may not only be used to actuate the injection tool, but may also serve to hold a reservoir for a substance that is to be injected. To this end, according to a further embodiment of the invention, the displacement device may be equipped with a mount in which the reservoir, such as e.g. the plunger of a syringe needle, can be inserted. With particular preference, the mount is equipped with an adjusting screw for metering the substance that is to be injected, as a result of which the injection quantity can be set in a precise and reproducible manner.

According to a further important feature of the invention, the injection device may be equipped with a sensor device which comprises one or more sensors for detecting the position of at least one of the guide, displacement and holder devices. Advantageously, the sensor device can provide signals for automatic adjustment of the parts of the injection device that can be displaced relative to one another, as a function of a predefined injection task.

The operational safety of the injection device according to the invention can advantageously be further increased if the holder device is equipped with a return spring which, if the displacement device can move freely, returns said displacement device to the pulled-back operating position. Advantageously, particularly in the case of a manually operated injection device, the displacement device is pushed forward counter to the effect of the return spring until the injection tool projects from the lumen of the guide device. When this manual forward force is removed, the return spring automatically returns the displacement device and thus retracts the injection tool into the lumen.

With regard to the method, the aforementioned objective is solved according to a further aspect of the invention by using the injection device according to the invention in such a way that firstly the guide device is positioned in the organism and then the displacement device is actuated to bring about the forward movement of the injection tool. Preferably, the positioning of the guide device also entails a positioning of an imaging probe which makes it possible to record an image of the desired injection site. Alternatively, the positioning of the imaging probe may take place independently of the injection device, with advantages being obtained in terms of a more compact design of the injection device and reduced stretching of the surrounding tissue.

If the actuation of the displacement device so as to introduce the injection tool as far as the injection site comprises a forward movement as far as the forward stop, the injection can advantageously be accelerated.

If, according to one preferred variant of the method according to the invention, the injection takes place using a syringe, the metering of the substance that is to be injected can be facilitated.

Further details and advantages of the invention will become apparent from the description of the appended drawings, in which.

Figure 1:
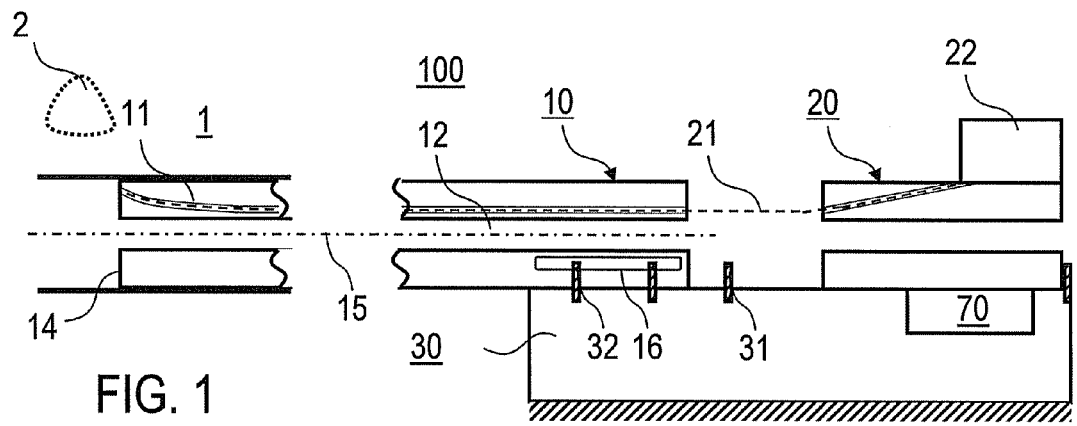
FIGS. 1 to 3 show schematic sectional views of various operating states of an injection device according to a first embodiment of the invention.

FIG. 1 illustrates a first embodiment of the injection device 100 according to the invention in a schematic sectional view. The injection device 100 comprises the guide device 10, the displacement device 20 and the holder device 30. Reference numeral 70 in FIG. 1 schematically denotes a sensor device which can be used to detect positions of the guide device 10 and of the displacement device 20 relative to the holder device 30. The sensor device 70 comprises for example optical sensors, by means of which bar-type markings on the guide and/or displacement devices can be detected.

The guide device 10 is a straight rigid tube with a lumen 11 and a channel 12. The tube has e.g. a semi-cylindrical shape with one flat side. The lumen 11 is provided for accommodating the injection tool 21 (shown in dashed line) and at the outlet end 14 of the guide device 10 is angled relative to the center line 15 of the guide device 10. In the illustrated embodiment, the channel 12 is provided for accommodating an imaging probe (shown in FIG. 2). The length of the guide device 10 is e.g. around 40 cm. For reasons of clarity, FIG. 1 does not show the entire length of the guide device 10 but rather an interruption is illustrated by the wavy line. The guide device 10 is arranged on the holder device 30 in a displaceable manner by means of a linear guide 16 (shown schematically).

The injection tool 21 is an injection needle which is attached to the displacement device 20. The displacement device 20 also carries a mount 22 for an injection reservoir (not shown), from which the substance that is to be injected can be introduced through the injection tool 21 to the injection site in the tissue. The displacement device 20 is arranged on the holder device 30 such that it can be displaced in a straight line in the manner of a slide, likewise by means of a linear guide (not shown).

The holder device 30 is equipped with a forward stop 31 which limits the forward movement of the displacement device 20. Furthermore, for the guide device 10 a backward stop 32 is provided which limits the backward movement of the guide device 10. When the displacement device 20 bears against the forward stop 31 and the guide device 10 bears against the backward stop 32, the injection tool 21 can project into the tissue of the organism 1 only as far as a predefined maximum depth. Injury to the adjacent tissue is ruled out.

FIG. 1 shows the injection device 100 in an operating state in which the guide device is introduced into a hollow organ, e.g. the urethra of a patient organism 1 to be treated. The guide device 10 is positioned in such a way that the outlet end 14 is at a predefined distance from the desired injection site 2 in the wall of the urethra. This distance is selected in particular as a function of the desired injection depth, as illustrated below. In the operating state shown in FIG. 1, the displacement device 20 is in the pulled-back operating position so that the injection tool 21 does not project from the lumen 11.

The positioning of the guide device 10 in the organism 1 according to FIG. 1 takes place under observation with an imaging probe 50, which for reasons of clarity is not shown in FIG. 1. The probe 50 is releasably fixed on the holder device 30 (see FIG. 2). It is held by the guide and displacement devices, which can be displaced relative to the probe 50.

Figure 2:
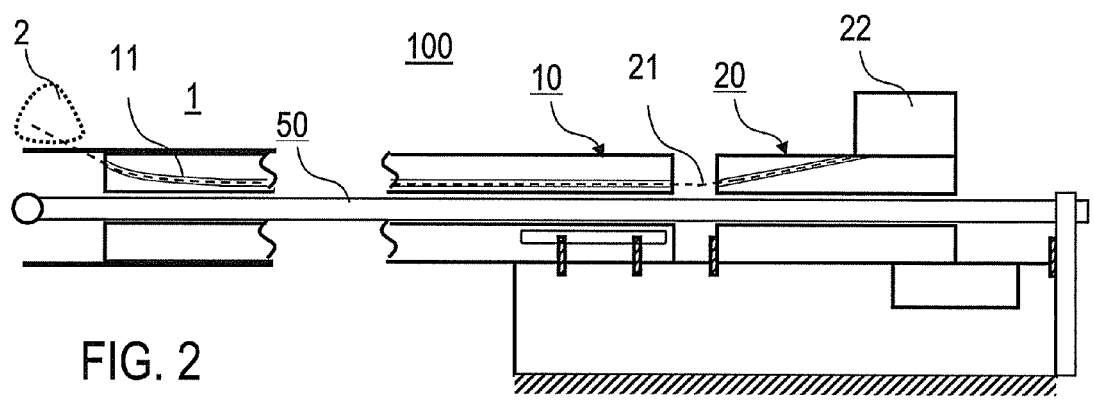

FIG. 2 illustrates the operating state of the injection device 100 with the injection tool 21 pushed forward. Due to the inclination of the lumen 11 relative to the longitudinal axis of the guide device 10, the end of the injection tool 21 projects into the tissue 2. In this state, an injection reservoir attached to the mount 22 is actuated in order to inject a substance into the tissue 2.

Figure 3:
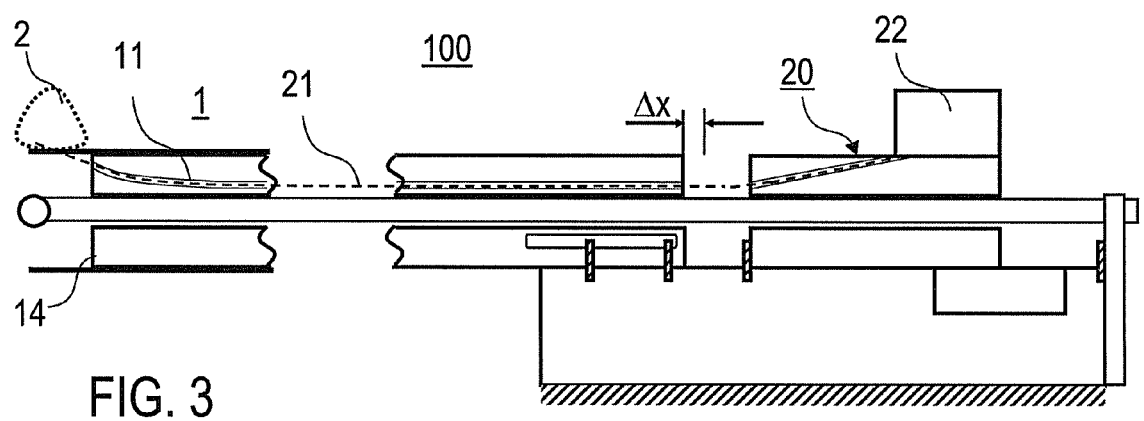

Like FIG. 2, FIG. 3 shows an operating state of the injection device 100 in which the injection tool 21 is pushed forward into the tissue 2. In this case, however, the guide device 10 is also pushed forward by a distance Δx, so that the distance of the outlet end 14 from the tissue 2 is reduced and thus the penetration depth of the injection tool 21 into the tissue 2 is reduced.

Figure 4:
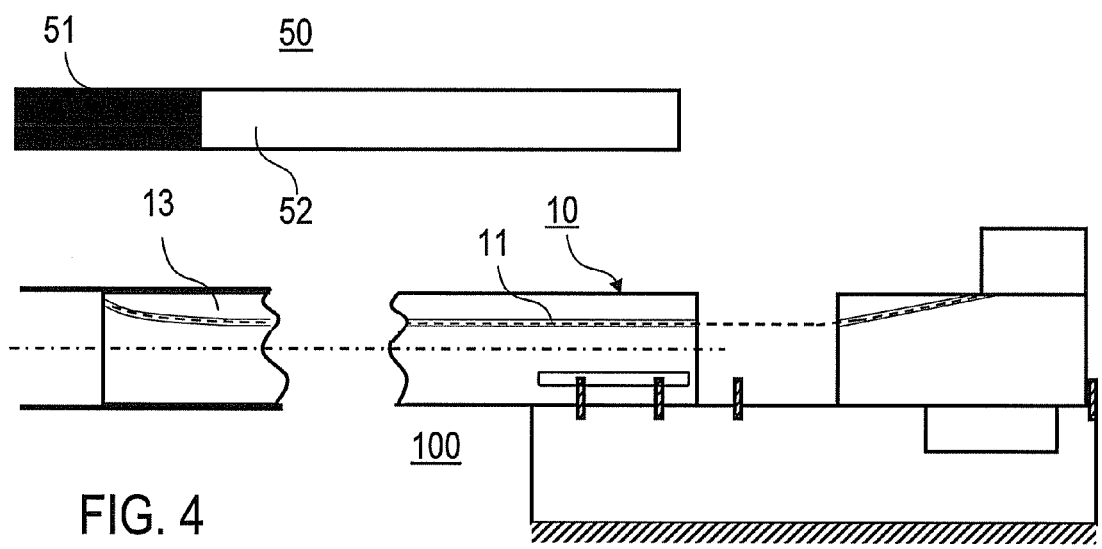
FIG. 4 shows a schematic sectional view of an injection device according to a further embodiment of the invention.

In order to implement the invention in practice, it is not necessary for the imaging probe 50 to be arranged in the channel 12. Alternatively, the imaging probe 50 (for example an ultrasonic probe or MRI probe) may be arranged separately from the injection device on the body surface (e.g. in order to record three-dimensional images) or in an adjacent body cavity. In this case, the channel 12 in the guide device 10 can be omitted. The guide device 10 is then a straight, rigid, rod-like component 13 which contains only the lumen 11 and is moreover compact, the imaging probe 50 with a sonic head 51 and a shaft 52 being oriented separately, as shown in FIG. 4.

Figure 5:
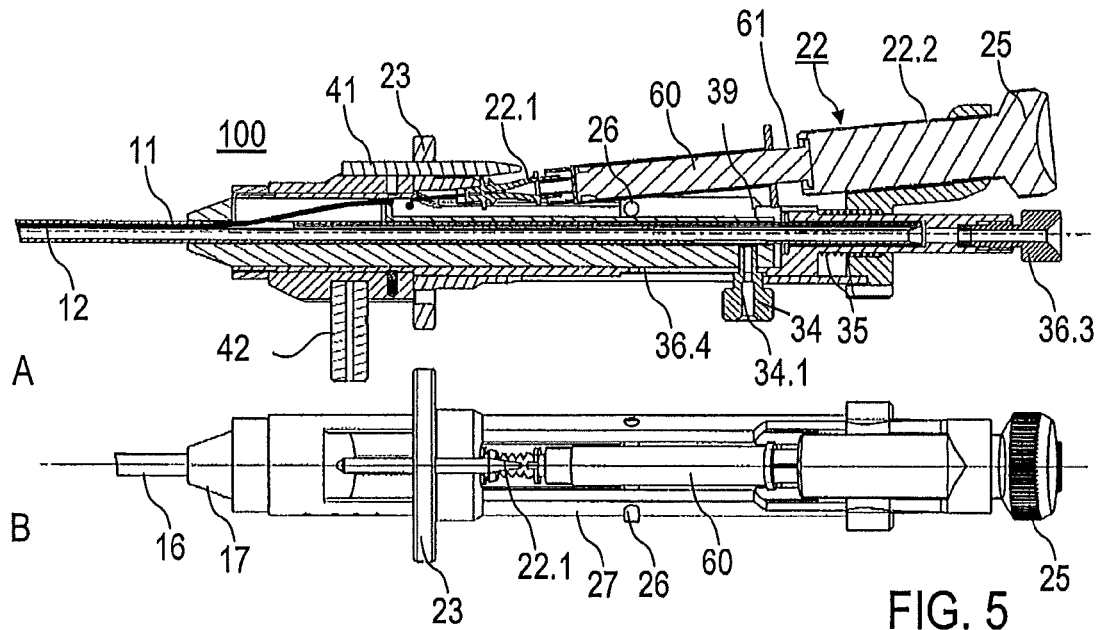
FIGS. 5A and 5B show a sectional view and a plan view of an injection device according to a further embodiment of the invention.

FIGS. 5A, 5B illustrate a modified embodiment of the injection device 100 according to the invention, which is preferably implemented on the basis of the compact design of the coaxial structure of the guide, displacement and holder devices.

Figure 9:

In the operating state shown in FIGS. 5A, 5B, the displacement device 20 is in the pushed-forward operating position. The sectional view shown in FIG. 5A and the perspective view shown in FIG. 9 show the guide device 10 with a straight molded tube 16, in which the lumen 11 and the channel 12 run. The channel 12 is provided for accommodating the imaging probe (not shown). For reasons of clarity, the figures do not show the entire length of the molded tube 16. Furthermore, the guide device 10 comprises a guide body 17, the outer diameter of which is adapted to the inner diameter of the tubular holder device 30.

Figure 8:
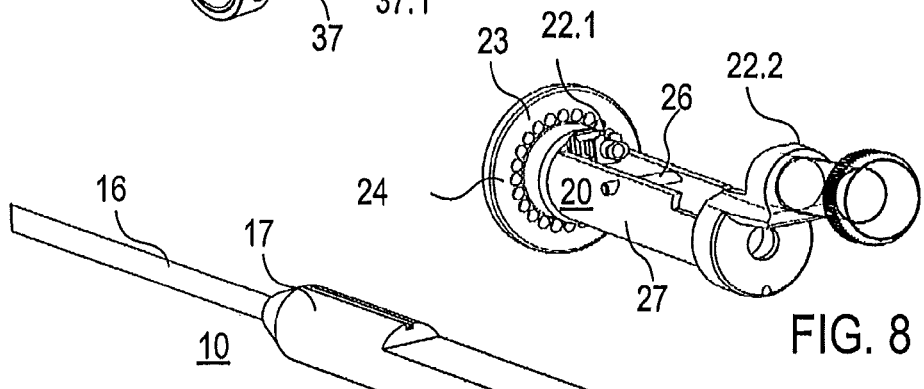

The displacement device 20 (see also FIG. 8) comprises a slide part 27 in the form of a cut-away hollow cylinder with a mantle surface that is open at the top and a transverse pin 26, which rests in a linear guide 38 of the holder device 30. The displacement device 20, to which the injection tool 21 is connected, furthermore comprises the mount 22 for the injection reservoir 60 and a perforated ring 23 with guide holes 24. In order to use the injection reservoir 60 in the form of a syringe, the mount 22 comprises a syringe attachment 22.1 and a plunger attachment 22.2, which can be adjusted by means of an adjusting screw 25. The inner diameter of the slide part 27 corresponds to the outer diameter of the cylindrical part 36 of the holder device 30 (see below). The slide part 27 can be displaced on the cylindrical part 36.

Figure 7:
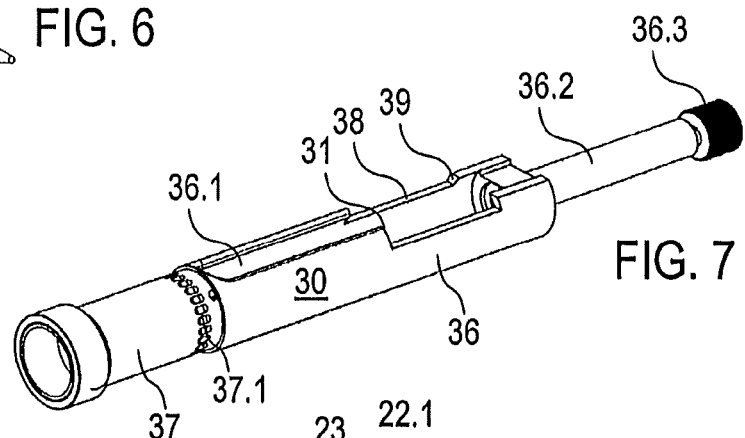

The holder device 30 (see also FIG. 7) comprises a cylindrical part 36 with a bearing part 37 and a guide sleeve 36.2. The surface of the cylindrical part 36 is cut away at the top in order to provide the linear guide 38 with a displacement path for the displacement device 20. The displacement path runs between the forward stop 31 and a rear stop 39. Furthermore, the surface of the cylindrical part 36 has an opening 36.1 for passing the injection tool 21 through to the guide device 10. Provided at the rear end of the guide sleeve 36.2 is a clamping screw 36.3 which can be used to fix the imaging probe in the channel 12 of the guide device 10. Furthermore, the guide sleeve 36.2 forms a support for a return spring 35, which is arranged between the rear end of the cylindrical part 36 and the rear end of the slide part 27. The return spring 35 is tensioned in the pushed-forward operating position of the displacement device.

Figure 6:
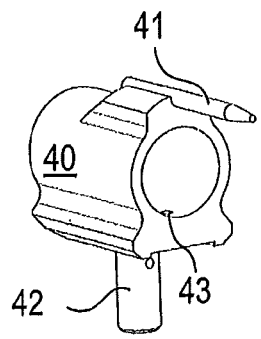
FIGS. 6 to 9 show schematic views of individual parts of the injection device shown in FIG. 5.

The bearing part 37 is seated in the rotary bearing 40 (see FIG. 6), which has a mandrel 41. The mandrel 41 cooperates with the perforated ring 23 of the displacement device 20. Furthermore, the rotary bearing 40 is fixedly equipped with a retaining bolt 42 for positioning it in a stationary manner on a stand (not shown). Located in the rotary bearing 40 is a latching protrusion, e.g. a spring-mounted ball 43, which cooperates with recesses 37.1 on the surface of the bearing part 37.

The cylindrical part 36 of the holder device 30 has on its underside a slot-shaped opening 36.4 (see FIG. 5A), by means of which the displacement path of the guide device 10 is defined. In order to temporarily fix the guide device 10 relative to the holder device 30, a clamping screw 34 with an internal flushing channel 34.1 is provided, through which flushing channel a tube can be placed for introducing a flushing fluid into the channel 12 of the guide device 10.

The injection using the injection device 100 according to the invention takes place in accordance with the following method. Firstly the holder device 30 with the rotary bearing 40 is positioned in a stationary manner relative to the organism 1, e.g. relative to the urethra of a patient. The tube 16 is introduced into the urethra, the introduction taking place in the pulled-back operating position of the displacement device 20 (transverse pin 26 against the rear stop 39) and under observation with the ultrasonic probe 50. The guide device 10 is positioned with its outlet end 14 (see FIG. 1) at a distance from the tissue 2 in such a way that, in the pushed-forward operating position of the displacement device 20 (transverse pin 26 against the forward stop 31), the injection needle in the pushed-forward position of the displacement device 20 will strike the desired injection site in the tissue 2. The manual movement of the displacement device 20 then takes place, so that the injection tool 21 is pushed forward. While the treating physician grips e.g. the retaining bolt 42 of the rotary bearing 40 and the perforated ring 23 with one hand, the adjusting screw 25 can be actuated with the other hand in order to move the syringe plunger 62 forward in the syringe 61. After injecting a predefined quantity, which is represented for example by a certain number of turns of the adjusting screw 25, the displacement device 20 is released. The displacement device 20 is then pulled back under the effect of the return spring 35 until the perforated ring 23 separates from the mandrel 41. In this situation, the holder device 30 with the guide device 10 and the displacement device 20 can be further rotated by one guide hole 24 and the displacement device 20 can be pushed forward again as far as the forward stop 31. In this position, the next injection takes place. This procedure is repeated until a complete rotation has been carried out. The holder device 30 is then pulled back, for example by displacing the rotary bearing 40 on the stand, in order to carry out a further radial injection into the urethra.

The features of the invention which are disclosed in the above description, the drawings and the claims may be important both individually and in any combination for implementing the invention in its various embodiments.

The invention claimed is:

1. An injection device for injecting a substance into an organism, comprising:
   a guide device with a lumen in which an injection tool is arranged in a displaceable manner, so that the injection tool is movable relative to the entire guide device,
   a displacement device to which the injection tool-is connected, and a holder device that forms a support for the guide and displacement devices, the guide and displacement devices being arranged on the holder device such that they can be displaced relative to one another and relative to the holder device, wherein:

the guide and displacement devices can be adjusted independently of one another on the holder device, the entire guide device is movable relative to the holder device, the lumen is angled relative to a center line of the guide device at an outlet end of the guide device, so that a free end of the injection tool leaving the outlet end moves away from the holder device in an injection direction having a radial component, and a penetration depth of the free end of the injection tool in the injection direction is determined by the adjustment position of the guide device relative to the holder device.

2. The injection device according to claim 1, in which the holder device has a forward stop which limits a forward movement of the displacement device relative to the holder device.

3. The injection device according to claim 1, in which the holder device has a backward stop which limits a backward movement of the guide device relative to the holder device.

4. The injection device according to claim 1, in which the holder device has a tubular structure and the guide device being arranged internally within the holder device and the displacement device being arranged externally on the holder device.

5. The injection device according to claim 1, in which the guide device and the displacement device are arranged such that they can be rotated about a longitudinal axis of the holder device.

6. The injection device according to claim 5, in which a rotary bearing is provided, in which the holder device with the guide device and the displacement device can be rotated about the longitudinal axis of the holder device.

7. The injection device according to claim 6, in which the rotary bearing has a mandrel which blocks a rotation of the holder device in a pushed-forward state of the displacement device.

8. The injection device according to claim 7, in which the displacement device has a perforated ring which cooperates with the mandrel of the rotary bearing.

9. The injection device according to claim 8, in which the perforated ring has guide holes, wherein at least one of a number and an angular distribution of the guide holes is selected as a function of the desired geometric distribution of the injection into the organism.

10. The injection device according to claim 1, in which the holder device has a first clamping device for fixing the guide device relative to the holder device.

11. The injection device according to claim 10, in which the first clamping device comprises a clamping screw with a flushing channel, through which a flushing fluid can be introduced into the guide device.

12. The injection device according to claim 1, in which the guide device has a channel for accommodating an imaging probe.

13. The injection device according to claim 12, in which the holder device has a second clamping device for fixing the probe in the channel.

14. The injection device according to claim 1, in which the displacement device has a mount for holding an injection reservoir.

15. The injection device according to claim 14, in which the mount for holding the injection reservoir has an adjusting screw for metering the substance that is to be injected.

16. The injection device according to claim 1, in which a sensor device is provided, which comprises at least one sensor for detecting the position of at least one of the guide, displacement and holder devices.

17. The injection device according to claim 1, in which the holder device has a return spring, by means of which the displacement device can be returned from a pushed-forward operating position.

18. A method for injecting a substance into an organism, use being made of an injection device according to claim 1, said method comprising the steps:

positioning the guide device on the holder device so that an outlet end has a predefined position relative to an injection site in the organism, actuating the displacement device so as to push the injection tool forward to the injection site, and injecting the substance by means of the injection tool.

19. The method according to claim 18, comprising the further step:

positioning an imaging probe in the guide device and recording an image of the injection site.

20. The method according to claim 18, comprising the further step:

positioning an imaging probe outside the injection device.

21. The method according to claim 18, in which the actuation of the displacement device comprises pushing it forward as far as the forward stop.

22. The method according to claim 18, in which the injection takes place using a syringe plunger which is attached to the displacement device.

23. The injection device according to claim 1, in which the displacement device has a pulled-back operating position, wherein the injection tool is pulled back toward the holder device, and a pushed-forward operating position, wherein the injection tool is pushed forward so that its free end leaves the lumen of the guide device, wherein the position of the guide device relative to the displacement device defines a free exit length and a penetration depth of the injection tool in the pushed-forward operating position of the displacement device.

* * * * *